United States Patent [19]

Ryan et al.

[11] Patent Number: 5,317,379
[45] Date of Patent: May 31, 1994

[54] CHEMICAL SPECIES OPTICAL ANALYZER WITH MULTIPLE FIBER CHANNELS

[75] Inventors: Frederick M. Ryan, New Alexandria; James W. Thomson, Murrysville, both of Pa.

[73] Assignee: Rosemount Analytical Inc., Eden Prairie, Minn.

[21] Appl. No.: 833,530

[22] Filed: Feb. 11, 1992

[51] Int. Cl.$^5$ .................. G01J 3/06; G01N 21/31; G01N 21/35
[52] U.S. Cl. ................ 356/308; 250/339.11; 356/328; 356/436
[58] Field of Search ........... 356/308, 326, 328, 419, 356/432, 436, 418, 319; 250/339

[56] References Cited

U.S. PATENT DOCUMENTS

| | | | |
|---|---|---|---|
| 3,055,258 | 9/1962 | Hurvitz | 356/308 |
| 3,805,196 | 4/1974 | Feichtner et al. | 330/30 R |
| 4,081,215 | 8/1978 | Penney et al. | 356/45 |
| 4,162,121 | 7/1979 | Starkweather et al. | 350/358 |
| 4,367,040 | 1/1983 | Goto | 356/44 |
| 4,477,190 | 10/1984 | Liston et al. | 356/418 |
| 4,490,845 | 12/1984 | Steinbruegge et al. | 382/1 |
| 4,505,550 | 3/1984 | Steinbruegge | 350/372 |
| 4,639,092 | 1/1987 | Gottlieb et al. | 350/372 |
| 4,652,756 | 3/1987 | Ryan et al. | 250/343 |
| 4,653,869 | 3/1987 | Gottlieb et al. | 350/372 |
| 4,663,961 | 5/1987 | Nelson et al. | 73/24 |
| 4,705,362 | 11/1987 | Ryan et al. | 350/372 |
| 4,707,605 | 11/1987 | Astheimer et al. | 250/347 |
| 4,736,103 | 4/1988 | Nelson et al. | 250/343 |
| 4,771,629 | 9/1988 | Carlson et al. | 73/23.1 |
| 4,883,963 | 11/1989 | Kemeny et al. | 250/339 |
| 4,915,500 | 4/1990 | Selkowitz | 356/221 |
| 4,950,077 | 8/1990 | Manabe | 356/328 |
| 4,958,896 | 9/1990 | Brinkmeyer et al. | |
| 5,039,855 | 8/1991 | Kemeny et al. | 250/339 |

FOREIGN PATENT DOCUMENTS

| | | | |
|---|---|---|---|
| 57-31037 | 8/1982 | Japan | 356/328 |
| 60-73343 | 4/1985 | Japan | 356/328 |
| PCT/US89/-05826 | 12/1989 | PCT Int'l Appl. | |

OTHER PUBLICATIONS

Nelson, "A Breakthrough in IR-AOTF Technology Makes Solid State Multi-gas Emission Monitoring Possible" *Proceedings of the American Power Conference*, vol. 48, pp. 356-364 (1986).

Harris et al., "Acousto-optic Photonic Switch", Optics Letters, vol. 14, No. 21 pp. 1177-1179 (Aug. 1989).

Stephens et al., "Demonstration of a Photonic Space Switch Utilizing Acousto-optic Elements", Optical Engineering, vol. 29, No. 3, pp. 183-190 (Mar. 1990).

Young et al., "Linear Array Acousto-optic Devices", IEEE Group of Sonics and Ultrasonics 1976 Ultrasonics Symposium, pp. 666-667 (Sep. 29-Oct. 1, 1976).

Coppock et al. "Wideband Optical Channelizer for Simultaneous Frequency and Direction Finding", The Society of Photo-Optical Instrumentation Engineers, Acousto-Optic Bulk Wave Devices, vol. 214, pp. 124-129 (Nov. 1979).

(List continued on next page.)

*Primary Examiner*—Vincent P. McGraw
*Attorney, Agent, or Firm*—Westman, Champlin & Kelly

[57] ABSTRACT

An analyzer measures properties of multiple chemical samples, and includes an optical filter element having a long axis and positioned at a location where simultaneous multiple light beams, corresponding to the chemical samples to be measured, form a diffuse light spot elongated along an axis which is substantially aligned with the filter element long axis. The analyzer also includes a light source, filter means incorporating the filter element for transmitting spectrally selected portions of the light beams, sample cell means for exposing each sample to its associated light beam, and detector means for detecting the light beams after modification by the samples and after transmission by the filter. In a preferred embodiment, optical fibers carry the light beams to and from the chemical samples.

23 Claims, 4 Drawing Sheets

OTHER PUBLICATIONS

Schmidtke et al., "NIR–Prozess-Spektrometer: Zusammensetzung von Gasen und Flüssigkeiten", Vdi-Berickte Nr. 509, pp. 293–295 (1984) (with English translation).

Schaefer et al., "Spektrodkipische Gas- und Flüssigkeits-Prozessmesstechnik", Technisches Messen Tm. 52 Jahrgang. Heft 6, pp. 233–241 (1986) (with English translation).

Vanderlugt et al., "Fresnel Transforms and Optical Computing", Optical and Hybrid Computing, SPIE vol. 654, pp. 51–56 (1986).

Rosemount Analytical Inc., "Multiple Component Liquid Process Spectrometer", Descriptive Bulletin 103-601, pp. 1–4 (Oct. 1989).

Harris, "Multichannel Acousto–optic Crossbar Switch", Applied Optics, vol. 30 No. 29, pp. 4245–4256, (Oct. 1991).

Infrared Fiber Systems, Inc., Specification sheet entitled "AOTF Spectrometer", one 2-sided sheet (Aug. 1991).

York Harburg bulletin entitled "Switchmaster", one 2-sided sheet (undated).

Harris, "Acousto–optic Photonic Switching", Thesis Submitted to North Carolina State University, pp. iv, v, 41–45, 82–98 (1990).

Wilson et al., "A Fiber Optic Matrix Switchboard using Acousto Optic Bragg Cells", Components of Fiber Optic Applications and Coherent Lightwave Communications, SPIE vol. 988, pp. 56–62 (1988).

CHEMICAL SPECIES OPTICAL ANALYZER WITH MULTIPLE FIBER CHANNELS

BACKGROUND OF THE INVENTION

This invention relates to chemical analyzing instruments, and more specifically to optical analyzing instruments for measuring properties such as the concentration of one or more chemical species in chemical samples.

Optical analyzing instruments which have a remote sample cell communicating with a central instrument unit via optical fibers are known. These instruments analyze a single chemical sample which can remain stationary or alternatively flow through the sample cell. However, such optical analyzing instruments are not well suited for measuring properties of a plurality of chemical samples provided simultaneously to the analyzer. Rather, an instrument for each sample is used. Using multiple instruments is complex, and differences in calibration can arise between the instruments which affect the analysis.

Other instruments make use of a mechanical translator for alternatively positioning fiber optic cables at a given location in order to effect multiple channel operation. However, instruments incorporating such translation devices typically suffer from reduced reliability and repeatability due to mechanical limitations such as wear.

The present invention is specially adapted to solve these and other problems associated with measuring properties of multiple chemical samples.

SUMMARY OF THE INVENTION

The improved analyzer utilizes a filter element having a long axis positioned at a location where light traveling simultaneously along multiple light paths, corresponding to the chemical samples to be measured, forms a diffuse light spot elongated along an axis. By the substantial alignment of the light spot axis with the filter element long axis, the analyzer utilizes a common filter element for the multiple light paths. The analyzer also includes a light source, filter means incorporating the filter element for transmitting spectrally selected portions of the light, sample cell means for exposing each chemical sample to light traveling along the corresponding light path to modify the light as a function of the properties to be measured, and detector means for detecting the light after modification by the chemical samples and after transmission by the filter means, the detector means providing detector outputs as a function of the properties to be measured. To the extent that the multiple channels utilize a common filter element as well as other potential common elements such as the light source and other components, the result is not only a more efficient and compact system, but one which has reduced calibration differences between the channels and reduced relative drift between the detector outputs since changes to the common system elements have substantially the same effect on all of the channels. Cost savings can also result from the use of these common, or shared, components.

In a preferred embodiment, the filter means is an acousto-optic tunable filter (AOTF) system, and the filter element is an AOTF crystal, such as tellurium dioxide, $TeO_2$. Transducer means preferably couples to the AOTF crystal to launch acoustic waves within the crystal such that the waves travel along the long axis of the crystal. Such an arrangement takes advantage of the relatively low-loss propagation of such waves through many AOTF crystals, thereby requiring less power consumption relative to the combined power consumption of individual transducer means used with each channel separately. This is an important benefit since reducing the power requirements of the AOTF system, and hence also of the analyzer, reduces undesired heating effects and increases reliability.

In another preferred embodiment, the transmission by the filter means of the spectrally selected portions includes transmission of a time sequence of spectral bands of the light. In this embodiment, the analyzer preferably further includes computing means for controlling the time sequence of spectral bands passed by the filter means and for computing analyzer outputs indicative of the concentration of a preselected chemical species. In this arrangement, the computing means also receives the detector outputs. The analyzer also preferably incorporates indicator means receiving the analyzer outputs for indicating the concentration of the preselected chemical species to an operator of the analyzer.

In still another preferred embodiment, the analyzer includes optical fiber means for carrying one or more light beams to and from corresponding sample cell means. This feature greatly enhances the flexibility of the analyzer by allowing the chemical samples to be remote from the main analyzer unit. Hence, multiple samples distant from one another can be analyzed with a single analyzer using optical fiber links.

DETAILED DESCRIPTION OF THE PREFERRED EMBODIMENTS

Figure 1:
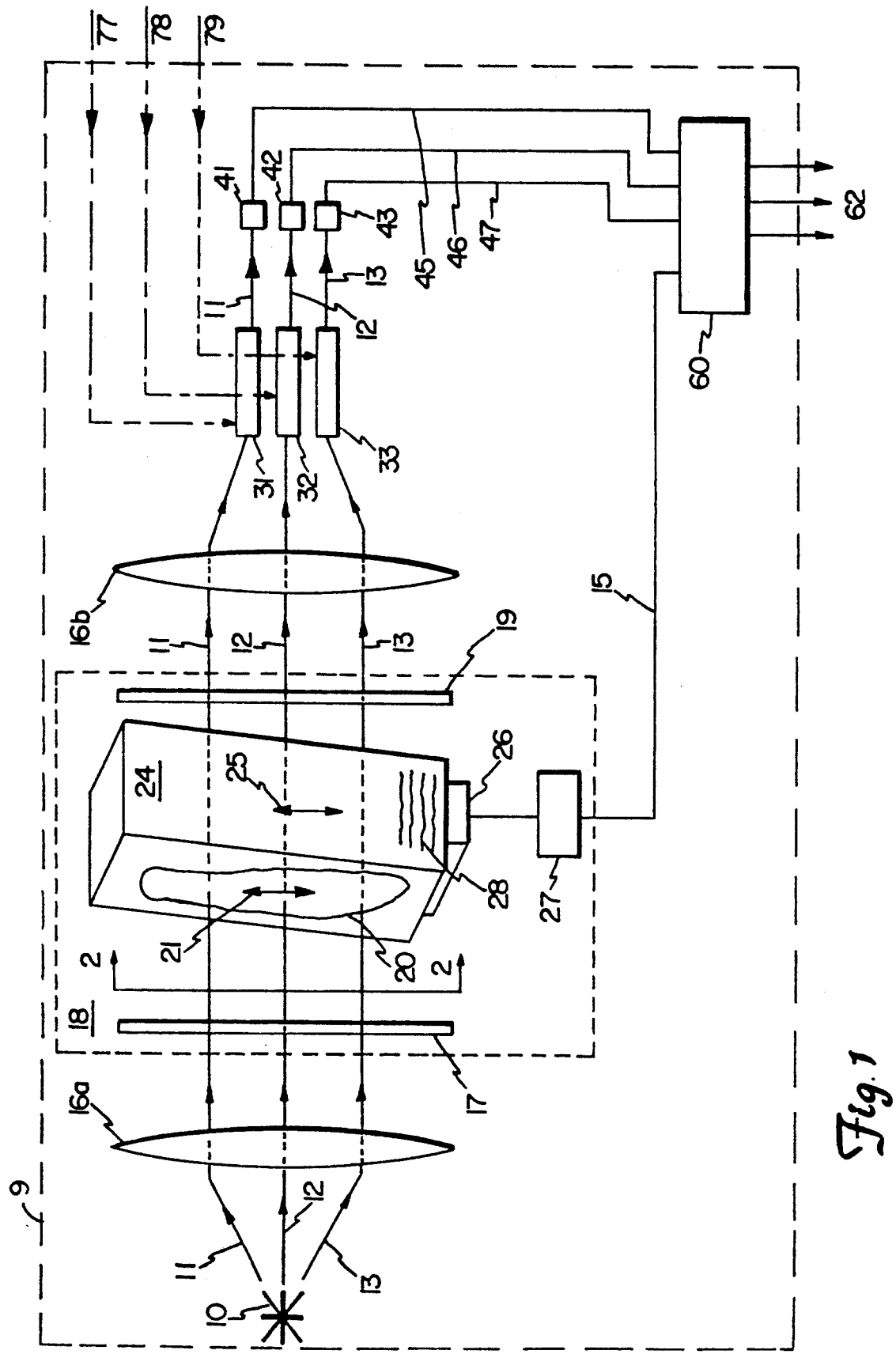
FIG. 1 is a block diagram of a first embodiment of an analyzer in accordance with this invention.

FIG. 1 shows an analyzer 9 in which light source 10 simultaneously projects polychromatic light along paths 11,12,13. Light source 10 preferably uses an extended filament incandescent bulb as a convenient means of providing the light. Light traveling along paths 11,12,13, which are shown schematically as single lines, can comprise substantially nonoverlapping distributions of light, or, more typically, overlapping light distributions wherein light associated with each path includes light rays emitted over a range of angles from a distinct region of light source 10. Alternately, light used in analyzer 9 can be described as simultaneously projected light beams, each light beam corresponding to light traveling along a given path. Shaping means 16a, comprising one or more lenses or mirrors, shapes the light into substantially collimated light having a cross-section which forms diffuse light spot 20. Diffuse light spot 20 has a shape which is elongated along a DLS (Diffuse Light Spot) axis 21 to accommodate multiple light paths 11,12,13. A tunable filter, shown in FIG. 1 as AOTF system 18, transmits spectrally selected portions of the light. AOTF system 18 includes a filter element, shown in FIG. 1 as AOTF crystal 24, positioned at diffuse light spot 20. The filter element has a shape elongated along a long axis 25 which is substantially aligned with DLS axis 21 to permit the use of a common filter element (i.e., AOTF crystal 24) with the multiple light paths. Typically, long axis 25 is substantially parallel to DLS axis 21. Shaping means 16b, comprising one or more lenses or mirrors, shapes the light transmitted by AOTF system 18 and directs it to sample cells 31,32,33, which hold chemical samples 77,78,79 (respectively) in either a stationary or a flow-through fashion. Chemical samples 77,78,79, as a function of the properties to be measured, operate on incoming light to yield light modified by such properties, which light is then converted to detector outputs at 45,46,47 by detectors 41,42,43. Detector outputs 45,46,47 are thus representative of the properties of chemical samples 77,78,79 (respectively) to be measured.

Each channel of analyzer 9, corresponding to each chemical sample, preferably analyzes the chemical sample according to well known differential absorption techniques to determine the concentration of one or more species within the sample. Accordingly, AOTF system 18 transmits a time sequence of spectral bands of the light at predetermined or programmed optical wavelengths. That is, AOTF system 18 preferably transmits light along paths 11,12,13 substantially simultaneously at a first wavelength, then at a second wavelength, and so on, so that light in all the channels is filtered in substantially the same spectral bands. Each chemical species within a chemical sample attenuates light in the spectral bands in a characteristic fashion and as a function of the concentration of such chemical species. Detectors 41,42,43 next detect the impinging light along paths 11,12,13, respectively, providing detector outputs at 45,46,47 varying with the impinging light intensity and thus also with the concentration of chemical species to be measured. Thermoelectrically cooled lead sulfide (PbS) detectors are preferred for use in infrared analyzer systems of the present invention due to their relatively low noise operation and convenience.

The preferred embodiment of the invention has particular benefits when analyzer 9 analyzes one or more same chemical species in all (or at least two) of the channels. In that case, the filter passes light in the programmed sequence of spectral bands, and the analyzer processes the detector outputs substantially simultaneously for all the channels, limited primarily by the speed of computing means within the analyzer. This simultaneous monitoring of all channels reduces the total time needed to measure the concentration of the desired chemical species in the samples. In contrast, analyzers employing a mechanical translator to effect multiple channel operation do not realize this benefit because they pass light through the samples sequentially rather than simultaneously.

Preferred tunable filters useable with the invention are those of solid state design which can have microscopic vibrations, but no parts moving relative to one another such as conventional rotating mirrors, motors, and so on. In this way the analyzer incorporates the benefits of reliability, repeatability, and stability of such devices. Another feature of tunable filters preferred for use in the invention is the ability to simultaneously filter light in all the light paths 11,12,13. This feature allows substantially continuous signal monitoring by each channel at detectors 41,42,43 to enhance signal-to-noise levels of detector outputs at 45,46,47. AOTF system 18 used as the tunable filter satisfies both of these criteria. As shown in FIG. 1, AOTF system 18 includes AOTF crystal 24 having long axis 25. Crystal 24 can be a uniaxial or biaxial material. Tellurium dioxide $TeO_2$ is preferred due to its optical and acousto-optical properties, and its availability as high quality single crystal. Transducer means 26, coupled or bonded to AOTF crystal 24, launches acoustic waves 28 in the crystal to interact with incident light to permit the filtering operation of AOTF system 18, as is known in the art. AOTF crystal 24 is made of a continuous piece of material to maintain good acoustic wavefront quality and minimize attenuation of acoustic waves 28. AOTF system 18 preferably operates in the anisotropic Bragg diffraction mode to enhance the angular acceptance of the filter means, thereby achieving enhanced light throughput from noncoherent polychromatic light sources. In anisotropic Bragg diffraction a spectral band of the incoming light, which has a first polarization state, is diffracted by acoustic waves 28 to yield the filtered output light having a second polarization state. In this mode, AOTF system includes crossed input and output polarizers 17 and 19, respectively, shown in FIG. 1. A conventional transducer circuit 27, in the process of driving transducer means 26 to produce acoustic waves 28, consumes and dissipates electrical power as a function of the physical size of transducer means 26. AOTF crystal 24 differs from an AOTF crystal useable in an equivalent single channel analyzer in that crystal 24 is longer in the direction along which acoustic waves are made to travel to accommodate the elongated portion of diffuse light spot 20. Because acoustic waves, once launched, propagate with low loss through AOTF crystal 24, transducer means 26 can have the same physical size as a transducer useable in an equivalent single channel analyzer, and thus transducer circuit 27 in analyzer 9 can consume and dissipate no more power than a transducer drive circuit of an equivalent single-channel analyzer. This is advantageous because reducing the power requirements of analyzer 9 reduces the weight and size of the analyzer, as well as reducing unwanted drift within the optical and/or electrical components of the analyzer due to reduced heat dissipated from transducer circuit 27. Heating effects are particularly undesirable in AOTF systems because changes in the AOTF crystal temperature produce changes in the wavelength of the light transmitted by AOTF system 18 for a given acoustic wave frequency.

As shown in FIG. 1, analyzer 9 also preferably includes computing means 60 receiving detector outputs 45,46,47 and coupled to AOTF system 18 over line 15 for controlling the time sequence of spectral bands and for computing analyzer outputs 62 indicative of the concentration of one or more chemical species within chemical samples 77,78,79. Computing means 60 selectively operates transducer circuit 27 to cause transducer 26 to launch acoustic waves 28 at selected frequencies, thereby causing AOTF system 18 to pass selected spectral bands or wavelengths of light along paths 11,12,13. As an example, with proper wavelength selection the ratio of detected intensities of two of the spectral bands provides a measure of acetic acid in a chemical sample. Analyzer 9, via computing means 60, accordingly provides outputs 62 indicative of the concentration of a desired set of chemical species for each chemical sample.

Figure 1A:
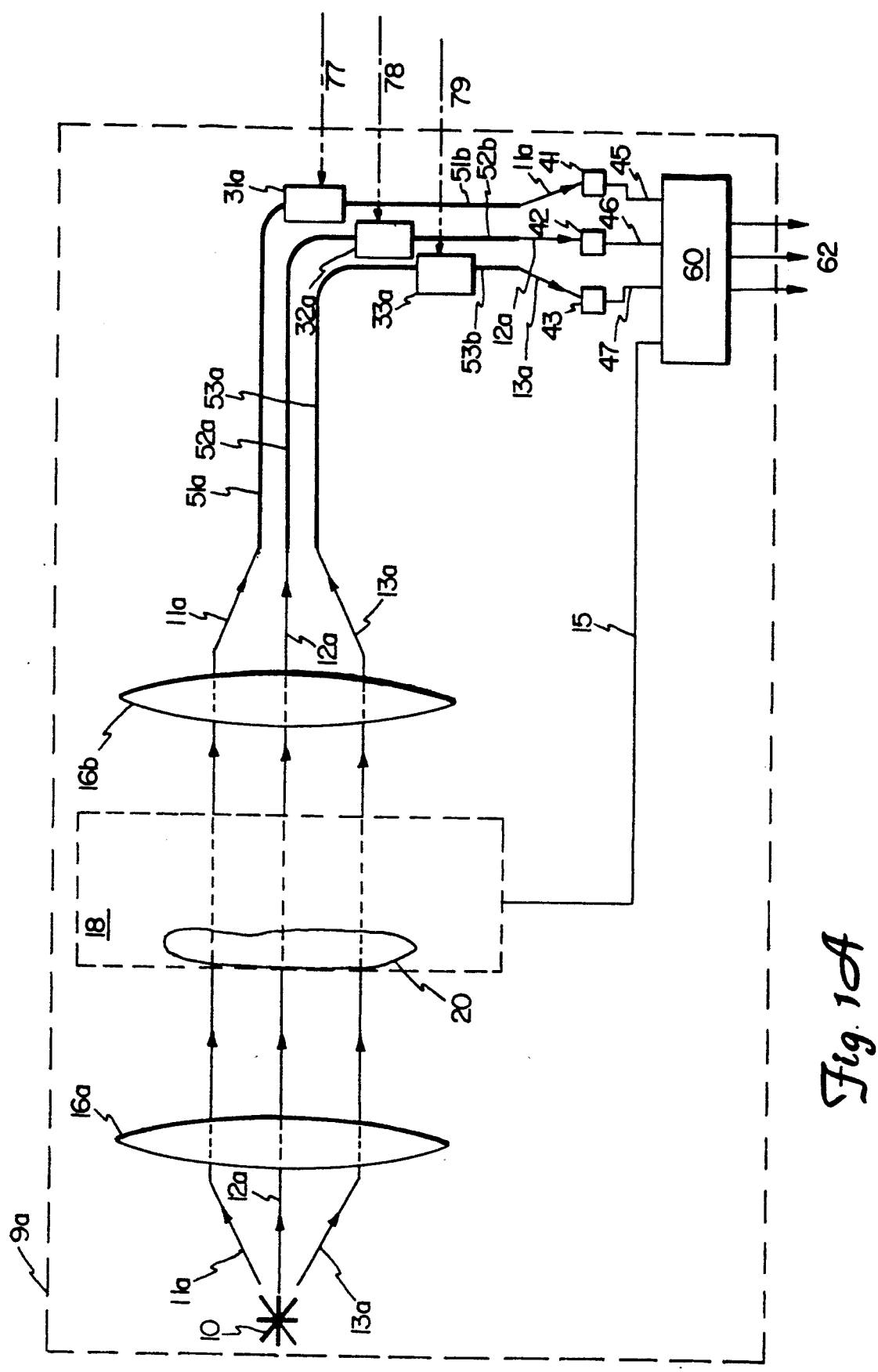
FIG. 1a is a block diagram similar to FIG. 1, but additionally including optical fibers for remote measurement applications.

FIG. 1a shows an analyzer 9a similar to analyzer 9 except that optical fibers 51a,52a,53a and 51b,52b,53b convey light to and from sample cells 31a,32a,33a. Light travels along paths 11a,12a,13a from light source 10 to detectors 41,42,43. Sample cells 31a,32a,33a are similar to cells 31,32,33, except that the former are additionally adapted to receive fiber inputs and to couple light from one fiber through the chemical sample to the other fiber. In an alternate embodiment (not shown), fibers 51b,52b,53b can be eliminated and fibers 51a,52a,53a can simultaneously carry the light traveling to the sample cells and the species modified light traveling away from the sample cells. In such case, sample cells 31a,32a,33a include reflectors to redirect light passing through the samples back into the same fiber. Further, the analyzer then additionally includes beamsplitting means for separating the species modified light from the light directed to the sample cells, and for directing the former to detectors 41,42,43.

Figure 1B:
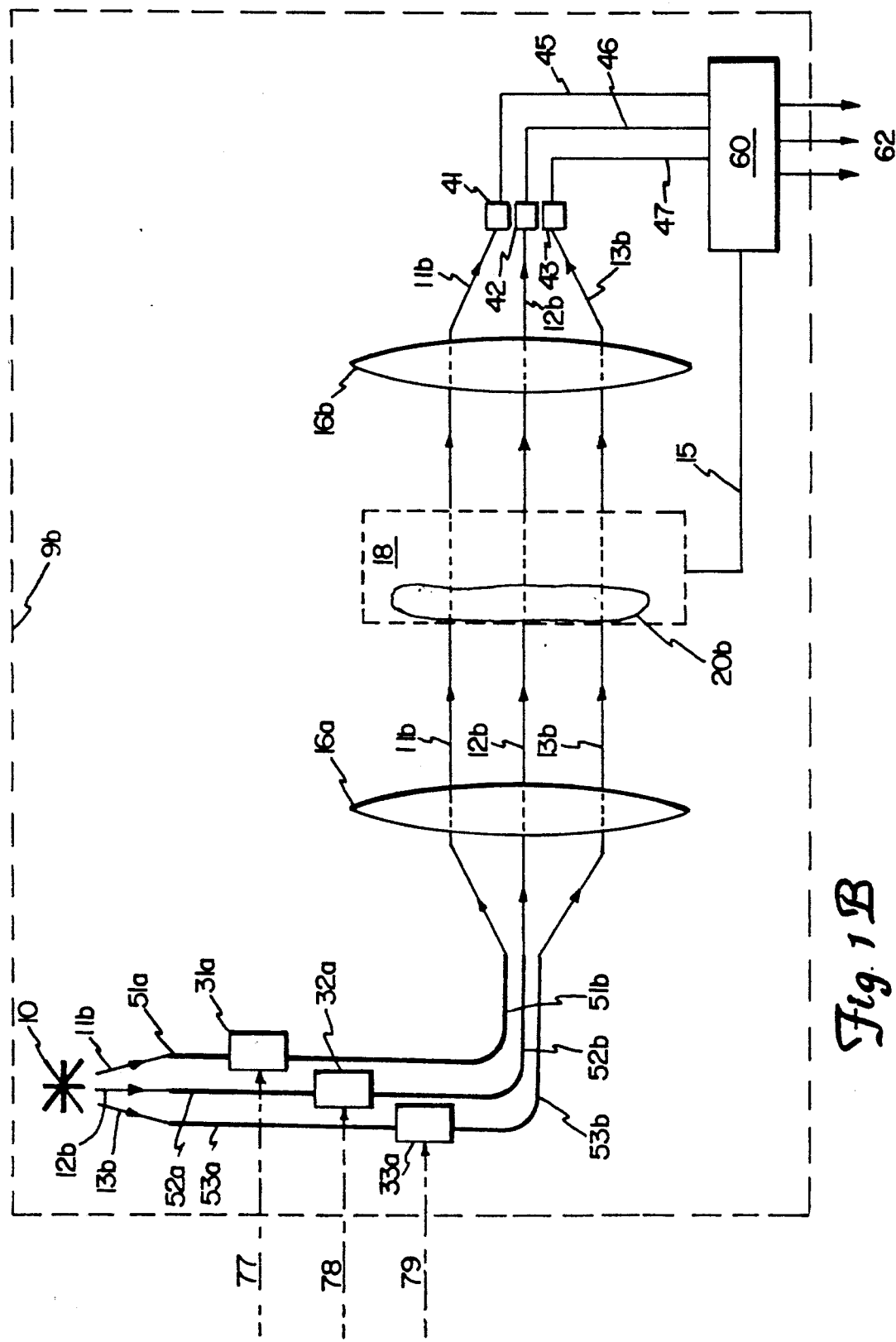
FIG. 1b is a block diagram similar to FIGS. 1 and 1a, but wherein the placement of the filter and sample cells is interchanged.

FIG. 1b shows an analyzer 9b similar to analyzers 9 and 9a except that the order of the tunable filter and sample cells is interchanged. Light travels from light source 10 to detectors 41,42,43 over light paths 11b,12b,13b. As with analyzer 9a, analyzer 9b utilizes optical fibers 51a,52a,53a and 51b,52b,53b. Chemical samples 77,78,79, as a function of properties to be measured, operate on impinging light traveling along paths 11b,12b,13b to yield species modified light, which is substantially collimated by shaping means 16a to form diffuse light spot 20b, similar to spot 20 except that the chemical samples have already modified the light forming the spot. Next, AOTF system 18 acts on the light as described previously to provide filtered light, which is then shaped by shaping means 16b and directed to detectors 41,42,43, which then convert the light in paths 11b,12b,13b into detector outputs 45,46,47 respectively.

Figure 2:
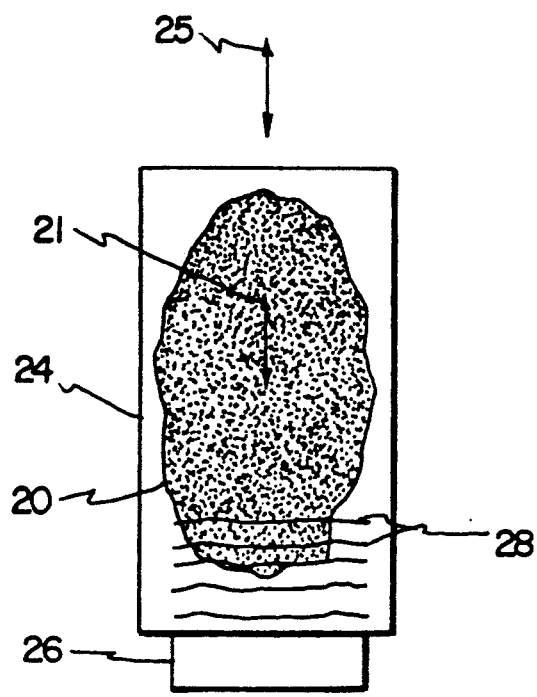
FIG. 2 is a view taken along line 2—2 in FIG. 1.

In FIG. 2, the view along line 2—2 of FIG. 1 is shown enlarged. AOTF crystal 24, shaped so as to define long axis 25, is substantially aligned with DLS axis 21 of diffuse light spot 20. Transducer means 26 launches acoustic waves 28 to travel along long axis 25. Acoustic absorbing means (not shown), known to those skilled in the art, are preferably held at the upper end of AOTF crystal 24, opposite transducer means 26, to absorb acoustic waves 228 after passage through the crystal.

Figure 3:
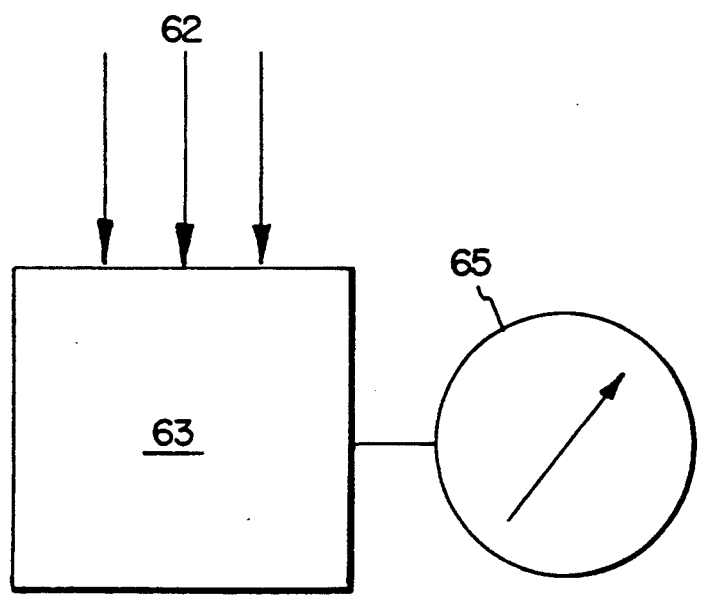
FIG. 3 is a block diagram of indicator means for use in optical analyzers of the present invention.

In FIG. 3, receiving circuit 63 accepts system outputs 62 from computing means 60 and modifies them such that indicator means 65, coupled to receiving circuit 63, displays one or more properties of the multiple chemical samples. Indicator means 65 displays, for example, concentration levels of selected species in samples 77,78,79 in an analog or digital fashion. Analyzers 9,9a,9b can include both receiving circuit 63 and indicator means 65.

Although the present invention has been described with reference to preferred embodiments, workers skilled in the art will recognize that changes can be made in form and detail without departing from the spirit and scope of the invention. For example, the order and placement of optical components can be changed within the scope of the invention. Although analyzers have been described having three channels, analyzers having two, four, or more channels also fall within the scope of the invention. Finally, the terms "light" and "optic(al)", when used herein, refer to not only visible light but electromagnetic radiation having wavelengths from about 100 nanometers to 100,000 nanometers.

We claim:

1. An analyzer for measuring properties of multiple chemical samples, comprising:
   a source simultaneously projecting multiple polychromatic light beams corresponding to the chemical samples;
   an AOTF system transmitting a time sequence of selected spectral portions of the light beams, the AOTF system including an AOTF crystal positioned at a location where a cross-section of the light beams forms a light spot elongated along a first axis, the AOTF crystal being sized so as to define a long axis substantially aligned with the first axis;
   sample cell means for exposing each chemical sample to its corresponding light beam to modify the corresponding light beam as a function of a property of the chemical sample; and
   detector means for detecting the light beams after modification by the chemical samples and after transmission by the AOTF system, the detector means providing detector outputs as a function to the properties being measured.

2. The analyzer of claim 1, wherein the light beams are transmitted by the AOTF system before modification by the chemical samples.

3. The analyzer of claim 1, wherein the light beams are transmitted by the AOTF system after modification by the chemical samples.

4. An analyzer as recited in claims 1, 2, or 3, wherein the source comprises an extended incandescent lamp.

5. The analyzer of claim 1, wherein the AOTF crystal comprises tellurium dioxide.

6. The analyzer of claim 1, wherein the ATOF system further includes a transducer coupled to the AOTF crystal for launching acoustic waves therein, and wherein the acoustic waves travel along the long axis of the AOTF crystal.

7. The analyzer of claim 6, wherein the analyzer further includes:
   optical fibers which carry the light beams to and from the sample cell means.

8. The analyzer of claim 1, further comprising:
   computing means, receiving the detector outputs and coupled to the AOTF system, for controlling the time sequence of spectral bands and for computing a measurement of each of the properties, corresponding to each chemical sample, as a function of the time sequence of the corresponding detector output.

9. The analyzer of claim 8, further including:
   indicator means coupled to the computing means for indicating the measurement of the property for at least one of the chemical samples.

10. An analyzer for measuring properties of multiple chemical samples, comprising:
    a source simultaneously projecting multiple polychromatic light beams corresponding to the chemical samples;
    an AOTF system transmitting a time sequence of selected spectral portions of the light beams, the AOTF system including an AOTF crystal disposed in the light beams;
    sample cell means for exposing each chemical sample to its corresponding light beam to modify the corresponding light beam as a function of the properties of the chemical sample;

detector means for detecting the light beams after modification by the chemical samples and after transmission by the AOTF system, the detector means providing detector outputs as a function of the properties; and computing means, receiving the detector outputs, for computing a measurement of each of the properties as a function of the time sequence of the corresponding detector output;

wherein the AOTF crystal has dimensions adequate to permit shared use of the AOTF crystal with the multiple light beams.

11. The analyzer as recited in claim 10, wherein the analyzer further includes:

optical fibers which carry the light beams to and from the sample cell means.

12. The analyzer as recited in claim 10, wherein the AOTF system operates in the anisotropic Bragg diffraction mode.

13. The analyzer as recited in claim 12, wherein the properties include a concentration of a preselected chemical species, and wherein the computing means is coupled to the AOTF system and controls the time sequence of selected spectral portions.

14. An analyzer for measuring properties of multiple chemical samples, comprising:

a source projecting light simultaneously along multiple light paths corresponding to the chemical samples, a cross-section of the light forming a light spot elongated along a first axis;

a filter transmitting a time sequence of selected spectral portions of the light, the filter being stationary relative to the source, and the filter including a filter element positioned at the light spot and so sized as to have a long axis substantially aligned with the first axis;

sample cell means for exposing each chemical sample to light traveling along the corresponding light path to modify the light as a function of the properties of the chemical sample; and a detection device detecting the light after modification by the chemical sample and after transmission by the filter, the detection device providing detector outputs as a function of the properties.

15. The analyzer of claim 14, wherein the light is transmitted by the filter before modification by the chemical samples.

16. The analyzer of claim 14, wherein the light is transmitted by the filter after modification by the chemical samples.

17. An analyzer as recited in claims 14, 15, or 16 wherein the source comprises an extended incandescent lamp.

18. An analyzer as recited in claims 14, 15 or 16, wherein the filter comprises an AOTF system, and the filter element comprises an AOTF crystal.

19. An analyzer as recited in claim 18, wherein the AOTF crystal comprises tellurium dioxide.

20. An analyzer as recited in claim 18, wherein the AOTF system further includes a transducer coupled to the AOTF crystal to launch acoustic waves therein, and wherein the acoustic waves travel along the long axis of the AOTF crystal.

21. An analyzer as recited in claim 20, wherein the analyzer further includes:

optical fibers which carry the light beams to and from the sample cell means.

22. An analyzer as recited in claim 21, wherein the properties include a concentration of a preselected chemical species, and wherein the analyzer further includes:

computing means, receiving the detector outputs and coupled to the AOTF system, for controlling the time sequence of selected spectral portions and for computing analyzer outputs indicative of the concentration of the preselected chemical species.

23. An analyzer as recited in claim 22, further including:

an indicator receiving the analyzer outputs and indicating the concentration of the preselected chemical species for at least one of the chemical samples.

* * * * *

UNITED STATES PATENT AND TRADEMARK OFFICE
CERTIFICATE OF CORRECTION

PATENT NO. : 5,317,379
DATED : May 31, 1994
INVENTOR(S) : Frederick M. Ryan et al.

It is certified that error appears in the above-indentified patent and that said Letters Patent is hereby corrected as shown below:

Column 4, line 19, "throughput" should read --throughout--.

Column 4, line 25, after "system" please insert --18--.

Column 6, line 24, cancel "to" and insert --of--.

Signed and Sealed this

Fifth Day of March, 1996

Attest:

BRUCE LEHMAN

Attesting Officer   Commissioner of Patents and Trademarks